United States Patent [19]

Lychou

[11] Patent Number: 6,000,102
[45] Date of Patent: Dec. 14, 1999

[54] APPARATUS FOR AIR-LAYING OF FIBROUS MATERIAL OR GRANULES

[75] Inventor: Claes Lychou, Hisings Backa, Sweden

[73] Assignee: SCA Molnlycke AB, Goteborg, Sweden

[21] Appl. No.: 09/110,199

[22] Filed: Jul. 6, 1998

[30] Foreign Application Priority Data

Jul. 3, 1997 [SE] Sweden .................................. 9702573

[51] Int. Cl.⁶ .................................................. D01G 25/00
[52] U.S. Cl. ............................ 19/296; 19/304; 198/689.1; 425/83.1
[58] Field of Search ............................. 19/296, 301, 303, 19/304, 305; 198/689.1; 264/518; 425/83.1, 363, 371

[56] References Cited

U.S. PATENT DOCUMENTS

| | | | |
|---|---|---|---|
| 3,736,081 | 5/1973 | Yovanovich | 425/371 |
| 3,883,285 | 5/1975 | DeMets | 425/371 |
| 4,306,934 | 12/1981 | Seppanen . | |
| 4,675,144 | 6/1987 | Hammond | 264/518 |
| 4,690,853 | 9/1987 | Hammond . | |
| 4,789,514 | 12/1988 | Lo | 425/363 |
| 5,200,129 | 4/1993 | Kobayashi et al. | 425/371 |
| 5,314,585 | 5/1994 | Ward . | |

FOREIGN PATENT DOCUMENTS

| | | |
|---|---|---|
| 1226039 | 7/1960 | France . |
| 2562106 | 10/1985 | France . |
| 168763 | 3/1905 | Germany . |
| 2069116 | 8/1981 | United Kingdom . |

*Primary Examiner*—Michael A. Neas
*Assistant Examiner*—Gary L. Welch
*Attorney, Agent, or Firm*—Young & Thompson

[57] ABSTRACT

An apparatus for air-laying of a material in the form of fibers or granules onto a running band. The apparatus includes at least one delimited space arranged at a first surface on an at least partially air-permeable endless running band. A vacuum exists in the space during operation and the band runs successively over the space. This takes place concurrently with air being sucked through the band into the space. At least two rotatable support elements are placed in the space in order to counteract down-bending of the running band. The support elements have a rotational direction generally coinciding with the running direction of the band.

9 Claims, 1 Drawing Sheet

APPARATUS FOR AIR-LAYING OF FIBROUS MATERIAL OR GRANULES

TECHNICAL FIELD

The present invention relates to an apparatus for the manufacture of an absorbent structure in an absorbent article, such as a sanitary napkin, a panty shield, an incontinence protector, a diaper, or the like, which is produced using an air permeable forming means in the form of an endless band, a so-called forming wire having a first side on which a vacuum pressure exists and onto which, within the same area but on the opposing side, absorbent material is deposited.

BACKGROUND OF THE INVENTION

Absorbent articles of the kind mentioned above, are known in a number of forms. Conventionally, the absorption core in such articles is produced by dry-defibration of cellulose pulp in the form of, for instance, rolls, bales or sheets and is converted in a fluffed form into a pulp web, sometimes with the admixture of so-called superabsorbents which are polymers having the ability to absorb several times their own weight of water or body fluid. The pulp core is often compressed, on the one hand to increase its fluid wicking capability and on the other hand to reduce the bulk of the absorbent core in order thereby to obtain an absorbent article which is as compact and demands as little space as possible.

In the technical field in question, it is common to use a vacuum pressure in order to deposit fibrous material onto a so-called forming wire, i.e. a kind of air permeable transport band, by supplying a mixture of air and absorption material to the wire wherein the air flows through the wire, thereby depositing its content of absorption core material onto said wire. Due to the fact that the layers of deposited material are air permeable per se, in this manner it is possible to deposit successive layers of material onto the forming wire, until the absorption core is formed.

U.S. Pat. No. 4,675,144 shows an apparatus for the formation of absorption cores, wherein a fibrous web is formed on an endless air-permeable band, a so called forming wire, as described above. Absorbent cores are then cut out from the formed fibrous web.

Further examples of apparatuses which employ the above mentioned technique are U.S. Pat. No. 4,739,910 and U.S. Pat. No. 4,690,853 which show a transport and folding device which utilise an air-permeable transport band, or a wire onto which absorption material is deposited, whereafter absorption cores are formed by means of a profiled, rotating brush.

When producing absorbent articles in accordance with the above mentioned method, it is usual to feed an air-permeable nonwoven material onto the forming wire such that the nonwoven material constitutes a carrier for the fibrous material which is deposited onto the forming wire. The nonwoven material, which may be elastic, will later constitute the sheet of material which is positioned closest to a wearer of the article. Further, in the technical field in question, it is known to use air-permeable, endless transport bands for pure transportation of different components, for instance between different manufacturing steps. One example of this is shown in U.S. Pat. No. 4,666,647.

A further example of a previously known technique is given in the Swedish patent application SE 9604803-8. This publication describes an apparatus for air-laying of a material in the form of fibres or granules onto an air-permeable, endless band wherein a second endless band is placed beneath the first band. The second endless band is designed with transverse bars which, on the one hand, define temporarily delimited spaces wherein vacuum exists, and on the other hand, provide a supporting force to the first endless band.

One problem with the use of all different types of air-permeable transport bands and forming wires is the relatively high friction which arises between the forming wire and the so called suction box. The suction box is the space, or spaces, at one of the surfaces of the forming wire, from where the evacuation of air takes place, whereby a vacuum pressure is created in the suction box. The suction box usually consists of a number of defining elements, such as wall elements and funnel-like evacuation elements. In addition, the suction box is delimited by the air-permeable endless band, i.e. the forming wire, which during operation is continuously moved past the suction box. Hereby, a certain amount of friction is created between the forming wire and its contact surfaces against the suction box, wherein the amount of friction depends, to a certain degree, on the size of the vacuum pressure which exists in the suction box. Neither is it unusual that small particles of absorption material which pass through the apertures in the air-permeable band are deposited onto the above-mentioned contact surfaces, whereby the friction is further increased.

The friction which arises, not only creates an increased energy consumption but also brings about an increase in temperature and a risk of operational problems due to an increased load on different components.

Furthermore, with the described type of equipment, it is necessary that the material which constitutes the transport band has a certain stiffness in order to counteract down-bending caused by the vacuum pressure which exists in the suction-box. This is normally solved by designing the transport band with a certain thickness and by placing a support plate, provided with a large number of holes, under the band which, accordingly, will slide on the plate. Another way is to substitute the support plate with supporting bars as in the above-mentioned Swedish patent application SE 9604803-8 which, however, requires a second endless band to carry the bars.

SHORT DESCRIPTION OF THE INVENTION

One objective with the invention is to offer an apparatus for air-laying of a material in fibrous or granule form onto a running band comprising at least one delimited space arranged on one side of an at least partially air-permeable endless band forming said running band, a vacuum existing in said space during operation, said band being intended to run continuously above said space. This takes place concurrently with air being sucked through said band into said space wherein said delimited space is defined by two long sides being generally coextensive with the running direction of said band and two short sides connecting said long sides and one bottom plate attached to said sides. The invention is characterised in that at least one rotatable support element is arranged in said space with the rotational direction of said rotatable support element generally coinciding with the running direction of said endless band.

The location of the rotatable support element is such that, at least when vacuum exists in the space, it will at least partly be in contact with the band in a supporting manner.

In this way, down-bending of the band is counteracted. The rotatable support elements may optionally be rotatably attached to axles which extend between the long sides, but rotatable support elements which are attached to or constitute parts of the axles which, in turn, are rotatable at their attachments to the long sides are also conceivable.

Since the support elements may rotate, either by being rotatably arranged on the axle or by the axle itself being rotatably arranged, the friction between the endless band and the support element will be minimal. Thereby, a desired reduction in energy consumption as well as in wear and heat development will be obtained. A further advantage with the present invention is that it can be applied to existing machinery without extensive reconstruction.

SHORT DESCRIPTION OF FIGURES

The invention will in the following be more closely described with reference to the embodiments which are shown in the appended drawings.

DETAILED DESCRIPTION OF EMBODIMENTS

Figure 1:
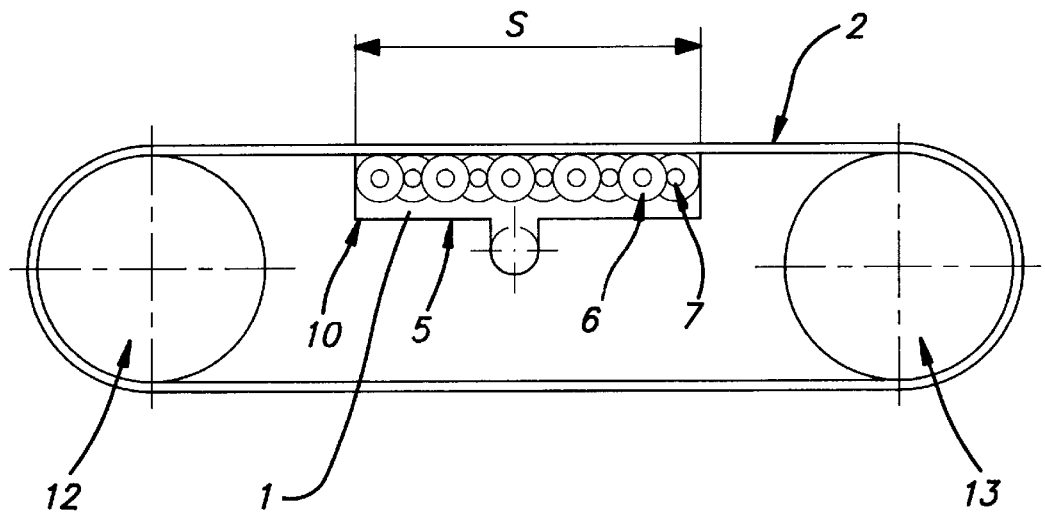
FIG. 1 shows a schematic side view of a so-called forming wire having a rotatable support element in accordance with the invention.
Figure 2:
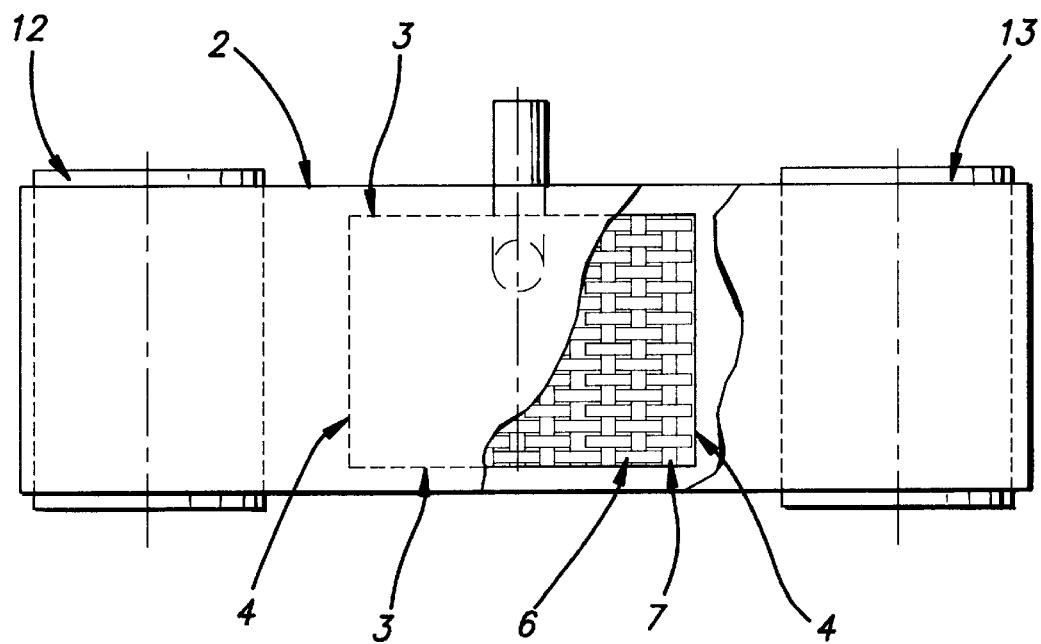
FIG. 2 shows the forming wire and the rotatable support element in FIG. 1 from above and with a portion of the forming wire cut away.

FIGS. 1 shows schematically a part of an apparatus for the formation of absorption bodies for absorbent articles. The apparatus according to the embodiment comprises an endless band 2 which is air-permeable at least within certain centrally arranged areas, for instance by being perforated, and which band is carried by two rollers 12,13 at least one of which being a driving roller. Beneath the endless band 2 is placed a so-called suction-box 10 which has an extension S in the direction of travel of the endless band 2. The suction-box 10 has two long sides 3,4 having an extension generally coinciding with the direction of travel of the band 2, and a bottom plate 5 attached to these sides 3,4. Furthermore, the suction-box 10 is provided with means for creating a vacuum pressure in the closed space 1 which is formed between the suction-box 10 and the endless band 2. Between the long sides 3 a number of axles 7 are arranged, which is most clearly shown in FIG. 2. On these axles a number of rotatable support elements 6 are arranged in the shape of rotatable wheels, both the axles 7 and the wheels 6 being adapted and placed so that they restrict down-bending of the endless band 2 when a vacuum pressure exists in the space 1. In the shown embodiment, the wheels 6 are placed in a staggered configuration, i.e. the center distance between two neighbouring axles 7 is less than the diameter of the wheels 6 and the axial distance between two neighbouring wheels 6 is greater than the width of the wheels 6.

In an alternative embodiment, the rotatable support elements 6 consist of encapsulated rotational bearings having the outer mantle surface of their outer rings in contact with the endless band 2 during operation.

In a further alternative embodiment, the axles 7 are rotatably attached to the long sides 3 and the support elements 6 are rigidly mounted onto the axles 7. The support elements 6 may also constitute a part of the axles 7.

The invention shall not be considered to be restricted to the above embodiments. Accordingly, the invention can be applied to other embodiments within the scope of the appended patent claims. Axles provided with support elements as above may, for instance, be arranged in existing suction-boxes on apparatuses of the disclosed type wherein the support plate may be removed.

I claim:

1. An apparatus for air-laying a fibrous or granulated material onto a running band, the apparatus comprising:
   an endless band that is at least partially air-permeable and has a first width in a direction transverse to a direction of movement of said endless band, said endless band being arranged and constructed to move continuously over a delimited space from which air is withdrawn, said space having one side defined by a moving surface of said endless band so that air moves through said endless band into said space during operation of the apparatus; and
   at least two rotatable support elements in said space that support said moving surface and at least two axles that are aligned in the transverse direction, each of said axles supporting at least one of said support elements, each of said support elements having a second width in the transverse direction that is less than said first width, centers of adjacent ones of said at least two axles being separated from each other by a distance that is less than a diameter of said support elements so that said support elements that are on adjacent ones of said at least two axles overlap each other in the transverse direction.

2. The apparatus of claim 1, wherein each of said axles supports at least two of said support elements and an axial distance between adjacent ones of said support elements on a same one of said axles is greater than said second width.

3. The apparatus of claim 2, comprising at least four of said axles and at least four of said support elements on each of said at least four axles.

4. The apparatus of claim 1, wherein said space is further defined by four walls, two of which extend in the transverse direction, and a bottom opposite said one side.

5. The apparatus of claim 1, wherein each of said support elements comprises a wheel and an encapsulated bearing rotatably supporting said wheel.

6. The apparatus of claim 1, wherein each of said support elements is rigidly attached to one of said axles.

7. The apparatus of claim 1, wherein said support elements tangentially contact said moving surface.

8. An apparatus for laying a material onto a running band, the apparatus comprising:
   an endless band that is at least partially air-permeable and that is arranged and constructed to move continuously over a delimited space from which air is withdrawn, said space having one side defined by a moving surface of said endless band so that air moves through said endless band into said space during operation of the apparatus, said one side of said space having a first width in a direction transverse to a direction of movement of said endless band; and
   a mat in said space and supporting said moving surface, said mat comprising a multiplicity of support wheels that each have a first diameter and a second width and a multiplicity of axles that are aligned in the transverse direction, each of said multiplicity of axles supporting a plurality of said support wheels that together extend across substantially all of said first width, adjacent ones of said support wheels on a same one of said axles being spaced from each other by a first distance that is greater than said second width, and centers of adjacent ones of said multiplicity of axles being separated from each other by a second distance that is less than said first diameter so that said support wheels that are on adjacent ones of said axles overlap each other in the transverse direction.

9. The apparatus of claim 8, comprising at least four of said axles and at least four of said support wheels on each of said at least four axles.

* * * * *